(12) United States Patent
Fujii

(10) Patent No.: US 11,226,243 B2
(45) Date of Patent: Jan. 18, 2022

(54) METHOD OF CALIBRATING TEMPERATURE SENSOR

(71) Applicant: Try and E Co., Ltd., Kobe (JP)

(72) Inventor: Takahiro Fujii, Kobe (JP)

(73) Assignee: Try and E Co., Ltd., Kobe (JP)

( * ) Notice: Subject to any disclaimer, the term of this patent is extended or adjusted under 35 U.S.C. 154(b) by 41 days.

(21) Appl. No.: 16/309,960

(22) PCT Filed: Mar. 2, 2018

(86) PCT No.: PCT/JP2018/008107
§ 371 (c)(1),
(2) Date: Dec. 14, 2018

(87) PCT Pub. No.: WO2019/026323
PCT Pub. Date: Feb. 7, 2019

(65) Prior Publication Data
US 2021/0223118 A1 Jul. 22, 2021

(30) Foreign Application Priority Data

Aug. 1, 2017 (JP) .............................. JP2017-149481

(51) Int. Cl.
*G01K 15/00* (2006.01)
*G01K 13/20* (2021.01)
*G01K 7/22* (2006.01)

(52) U.S. Cl.
CPC .............. *G01K 13/20* (2021.01); *G01K 7/22* (2013.01); *G01K 15/005* (2013.01)

(58) Field of Classification Search
CPC .... G01K 15/005; G01K 1/024; G01K 15/007; G01K 15/00; G01K 13/20; G01K 7/22;
(Continued)

(56) References Cited

U.S. PATENT DOCUMENTS 4,475,823 A * 10/1984 Stone .................... G01K 15/005
374/1
7,731,418 B2 * 6/2010 Price ...................... G01K 15/00
374/1
(Continued)

FOREIGN PATENT DOCUMENTS

CN 205144530 U * 4/2016
CN 09656181 U * 11/2019
(Continued)

*Primary Examiner* — Gail Kaplan Verbitsky
(74) *Attorney, Agent, or Firm* — J-Pat U.S. Patent Legal Services; James Judge

(57) ABSTRACT

Temperature-sensor calibrating method enables a wireless-data-communicating wearable clinical thermometer to be reused. The thermometer's temperature sensor, for sensing and measuring a target subject's body temperature, is detachable from/reattachable into a main unit of the thermometer. The temperature sensor is calibrated whenever it is to be swapped out, making thermometer main unit post-multicycle-use disposable. The calibration is accomplished by sampling and acquiring a base resistance value per the temperature sensor, computing, based on the difference between the acquired base resistance value and a resistance value gauged with a standard temperature gauge, a calibration coefficient, storing the calibration coefficient in a measuring-device storage medium, and transmitting the calibration coefficient to the thermometer main unit.

11 Claims, 5 Drawing Sheets

(58) Field of Classification Search
CPC ............ A61B 5/01; A61B 2018/00791; A61B 2560/0223; A61B 5/7221; A61B 2017/00725; G01J 5/0265; G01J 5/0025; G01J 2005/0051; G01J 5/20; H04M 1/0258

USPC ............... 374/1–3, 121, 120, 185, 163, 100; 702/99; 340/870.17

See application file for complete search history.

(56) References Cited

U.S. PATENT DOCUMENTS

| | | | | |
|---|---|---|---|---|
| 8,600,693 | B1* | 12/2013 | Kennamer | G01K 1/024 702/99 |
| 8,702,306 | B2* | 4/2014 | Mowry, Jr. | G01K 15/005 374/179 |
| 8,974,115 | B2* | 3/2015 | Segal | A61B 5/01 374/1 |
| 9,599,521 | B2* | 3/2017 | Yarden | G01K 13/20 |
| 2005/0226310 | A1* | 10/2005 | Nakazawa | G01K 13/20 374/208 |
| 2006/0122473 | A1* | 6/2006 | Kill | G01K 1/024 600/300 |
| 2010/0268056 | A1* | 10/2010 | Picard | A61B 5/6807 600/388 |
| 2011/0048547 | A1* | 3/2011 | Hasson | H05B 1/02 137/341 |
| 2011/0245633 | A1* | 10/2011 | Goldberg | A61B 5/165 600/301 |
| 2012/0057615 | A1* | 3/2012 | Weng | G01J 5/025 374/128 |
| 2013/0185213 | A1* | 7/2013 | Insanic | G06Q 20/32 705/73 |
| 2013/0315276 | A1* | 11/2013 | Segal | H04M 1/0258 374/1 |
| 2014/0112368 | A1* | 4/2014 | Engelstad | G01K 15/005 374/1 |
| 2014/0219316 | A1* | 8/2014 | Tashiro | G01K 7/22 374/185 |
| 2016/0057268 | A1* | 2/2016 | Jiang | H04B 1/385 455/556.1 |
| 2016/0268647 | A1* | 9/2016 | Umemura | H02J 7/0091 |
| 2018/0070824 | A1* | 3/2018 | Cronin | A61B 5/0022 |
| 2018/0184908 | A1* | 7/2018 | Meyerson | G01K 7/427 |
| 2019/0313907 | A1* | 10/2019 | Khachaturian | A61B 5/02416 |
| 2019/0328327 | A1* | 10/2019 | Kim | G01J 1/429 |
| 2019/0339221 | A1* | 11/2019 | Bhavaraju | G01N 27/3274 |
| 2020/0205662 | A1* | 7/2020 | Lee | H04W 12/06 |
| 2021/0251720 | A1* | 8/2021 | Jhaveri | A61B 90/98 |

FOREIGN PATENT DOCUMENTS

| | | | |
|---|---|---|---|
| CN | 111521286 A | * | 8/2020 |
| JP | S57-011634 A | | 1/1982 |
| JP | S58-116644 U | | 8/1983 |
| JP | 11044779 A | * | 2/1999 |
| JP | 2003-270051 A | | 9/2003 |
| JP | 2005-140629 A | | 6/2005 |
| JP | 2013-072733 A | | 4/2013 |
| JP | 2013-134224 A | | 7/2013 |

* cited by examiner

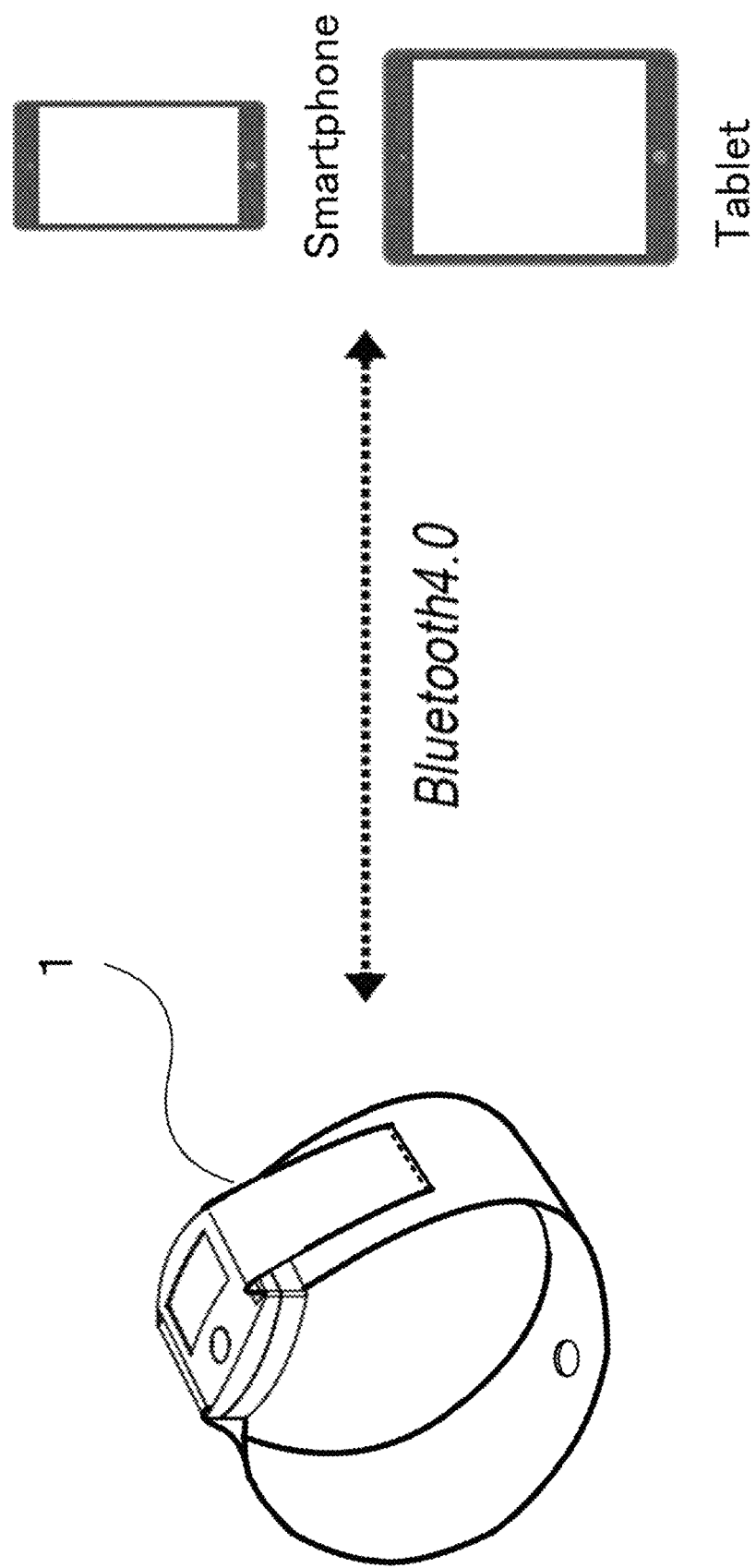

METHOD OF CALIBRATING TEMPERATURE SENSOR

TECHNICAL FIELD

The present invention relates to a method of calibrating a temperature sensor detachably/reattachably fitted into a wireless data-communicating clinical-thermometer main unit, for sensing a target subject's body heat to measure his/her temperature.

BACKGROUND ART

In hospitals and other medical institutions, patients' body temperatures are periodically measured, and the measurement results are administered. Generally, in measuring body temperature, the thermometer is applied to a measurement region on the examinee, who for a fixed period of time until the measurement finishes is kept in a still state, and when the measurement finishes the measurer checks and records the measurement result. In cases where the examinee is an infant or a seriously ill patient, however, continuing to apply the thermometer to the measurement region can be challenging, such that carrying out an accurate body-temperature measurement is not a simple matter; what is more, with newborn babies and infants, at times, such as during the night, when the body temperature abruptly changes, the changes must be grasped objectively by chronologically gauging the body temperature. Moreover, the job of checking and recording the measurement results places a high burden on the measurer, such that lightening the load on the measurer has been desired.

While interest in medical technologies that take advantage of portable computers, smartphones, and tablet computers has been on the rise in recent years, so-called wearable devices for gauging body temperature have already been developed, whereby checking and recording, via wireless communication means, measurement results of having gauged body temperature has become possible.

As to the body-temperature measurement/recording device set forth in Patent Document 1, a body-temperature logging patch ("patch" in the following)—a wearable clinical thermometer—that chronologically accumulates a patient's body temperature in a memory is proposed. With this body-temperature measurement device, the patch can be fitted onto the body of a patient—for example, onto the forehead, trunk, arms, legs, or other location on the body—and through a plurality of sensors a plurality of temperatures in the same positions or in different positions on the patient may be sensed, and further, via a wireless communication means, checking and recording measurement results of having gauged body temperature is possible.

PRECEDENT TECHNICAL LITERATURE

Patent Documents

Patent Document 1: Japanese Nat'l. Stage App. Pub. No. 2016-505808

SUMMARY

Issues Invention is to Address

Nevertheless, the patch involving Patent Document 1 is a disposable product, and for the user, making it disposable puts the cost high. Therein, an object of the present invention, taking the above-described circumstances into consideration, is to make available a temperature-sensor calibrating method that enables a wearable clinical thermometer to be reused by having its temperature sensor be detachable from/reattachable into the clinical-thermometer main unit, and by calibrating the temperature sensor whenever the temperature sensor is to be swapped out, making it possible to render the clinical-thermometer main unit post-multi-cycle-use disposable.

Means for Resolving the Issues

In order to accomplish the just-stated objective, a temperature-sensor calibration method involving the present invention comprises a base-resistance acquisition step of sampling a base resistance value per a temperature sensor, fitted detachably from/reattachably onto a wireless-data-communicating wearable clinical thermometer, for sensing a target subject's body temperature and measuring the temperature, and of acquiring the base resistance value, a computation step of computing, based on the difference between the acquired base resistance value and a resistance value gauged with a standard temperature gauge, a calibration coefficient for calibrating temperature, and a storage step of storing the calibration coefficient in a measuring-device storage medium, and is characterized in that the calibration coefficient is transmitted to the clinical-thermometer main unit.

Herein, a computing device and a memory device are built into the clinical-thermometer main unit, which may be configured such that in the computing device, based on the transmitted calibration coefficient, relationships between base resistance values and actual temperatures are computed to prepare a resistance-temperature conversion table, and such that the resistance-temperature conversion table is stored in the memory device. With such a table having been prepared, the clinical-thermometer main unit when measuring can obtain a figure for the actual temperature without making the computation every time, but simply by referring to the table, which therefore can serve to curtail the time till the temperature is displayed and reduce costs.

Further, the configuration may be rendered to calculate the relationships between base resistance values and actual temperatures based on calibration coefficients estimated beforehand, to prepare a plurality of resistance-temperature conversion tables. A plurality of tables having thus been prepared makes it possible to select an optimal resistance—temperature conversion table corresponding to the calibration coefficient transmitted from the temperature sensor.

Further, in cases where a single resistance-temperature conversion table is prepared and stored, re-preparing it by performing computations in accordance with the calibration coefficient, and storing the table in a rewritable storage device is desirable.

The temperature sensor advantageously is an NTC thermistor. Further, sampling of the base-resistance value is favorably carried out within a constant-temperature bath at 37° C. Still further, the calibration coefficient may be computed utilizing the thermistor's B constant.

The clinical-thermometer main unit may be furnished with a wireless communications transceiver, which may be configured so that transmission of the calibration coefficient to the thermometer main unit employs a standard NFC communication protocol, or may configured so that it employs a standard Bluetooth (registered trademark) communications protocol.

Effects of Invention

According to a temperature-sensor calibration method involving the present invention, reuse of a wearable clinical thermometer is made possible, in implementations having the temperature sensor be detachable from/reattachable into the clinical-thermometer main unit, by calibrating the temperature sensor whenever the temperature sensor is to be swapped out, enabling the clinical-thermometer main unit to be rendered post-multicycle-use disposable.

BRIEF DESCRIPTION OF DRAWINGS

FIG. 3 is a schematic diagram representing, in a wireless communications transceiver of the thermometer main unit, a system for receiving body-heat measurement temperatures.

MODES FOR EMBODYING INVENTION

In the following, based on the drawings, a detailed description of modes of embodying the present invention will be made. In each figure, identical parts are labeled with identical reference numbers, such that reduplicating description will be omitted. Further, the drawings in some instances are expressed exaggeratedly for the sake of understanding the present invention, wherein it should be borne in mind that they are not necessarily scaled-down, minute representations. Also, the present invention is not limited to the embodying modes discussed below.

Embodiment Example 1

Embodiment Example 1 will be described in detail with reference to the drawings.

The fact that, as stated above, there are individual differences in the characteristics of electronic clinical thermometers makes it necessary to establish calibrations (compensations) that is, coefficients, etc. in a polynomial approximating function—for electronic clinical thermometers severally on a per-device basis, and to write the calibrations into a built-in memory. Conceivable as a method of establishing calibration constants among the coefficients, etc. would be to place individual electronic clinical thermometers under a plurality of differing environments and on every occasion a detection signal is output from an electronic thermometer's sensor, send it to a computer, and thereafter signal-process the data from the several electronic thermometers to find calibration coefficients and write the calibration coefficients into a built-in memory. Nevertheless, even with thermistors of identical specification standards, there are variations in the B constant, because of which it is challenging to maintain accuracy in a broad environmental temperature range. For example, letting a range of human-body temperature measurements with an electronic thermometer's thermistor be 34-42° C., then the accuracy of the thermistor should be maintained throughout a range of 8° C. Herein, the "B constant" is a constant representing the magnitude of change in resistance found from temperatures in two arbitrary points with resistance-temperature characteristics. With thermistors, according to the way in which the resistance value changes, there are negative temperature coefficient (NTC) thermistors and positive temperature coefficient (PTC) thermistors, wherein with NTC thermistors when the temperature rises the resistance falls, and with PTC thermistors up until a given temperature the resistance is constant and at the boundary of the given temperature the resistance abruptly rises.

In Embodiment Example 1, the temperature sensor 20 utilized in the wearable clinical thermometer 1 will be described on the premise that an NTC thermistor is utilized.

Figure 1:
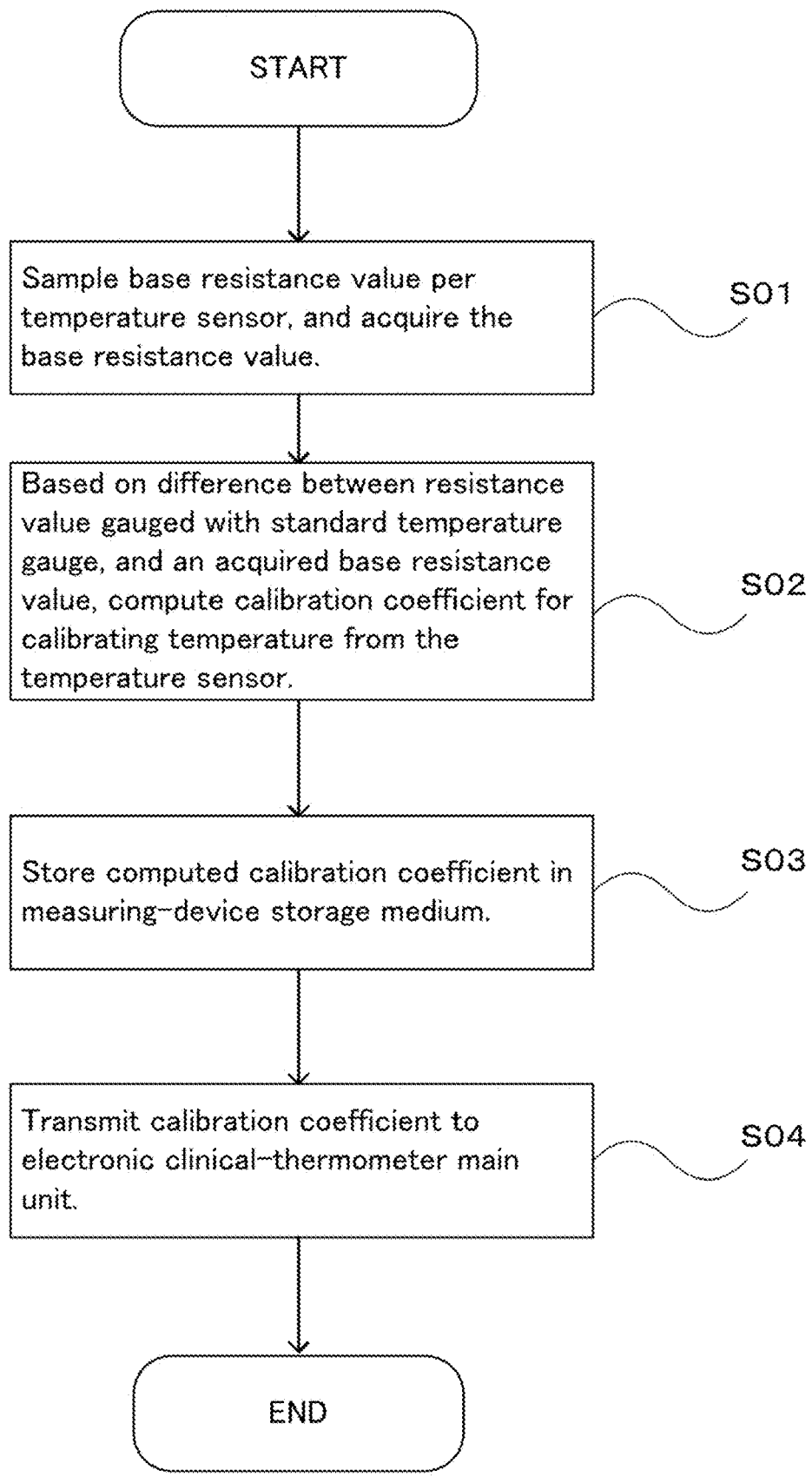
FIG. 1 is a flowchart of a temperature-sensor calibration method involving the present invention.

Reference is made to FIG. 1. FIG. 1 is a flowchart of a method, involving the present invention, of calibrating a temperature sensor 20. As indicated in FIG. 1, the temperature-sensor 20 calibration method involving the present invention comprises: a base-resistance acquisition step (S01) of sampling a base resistance value per a temperature sensor, fitted detachably from/reattachably onto a wireless-data-communicating wearable clinical thermometer 1, for sensing a target subject's body temperature and measuring the temperature, and of acquiring the base resistance value, a computation step (S02) of computing, based on the difference between the acquired base resistance value and a resistance value gauged with a standard temperature gauge, a calibration coefficient for calibrating temperature, and a storage step (S03) of storing the calibration coefficient in a measuring-device storage medium, and is characterized in that (S04) the calibration coefficient is transmitted to the clinical-thermometer main unit.

Figure 2A:
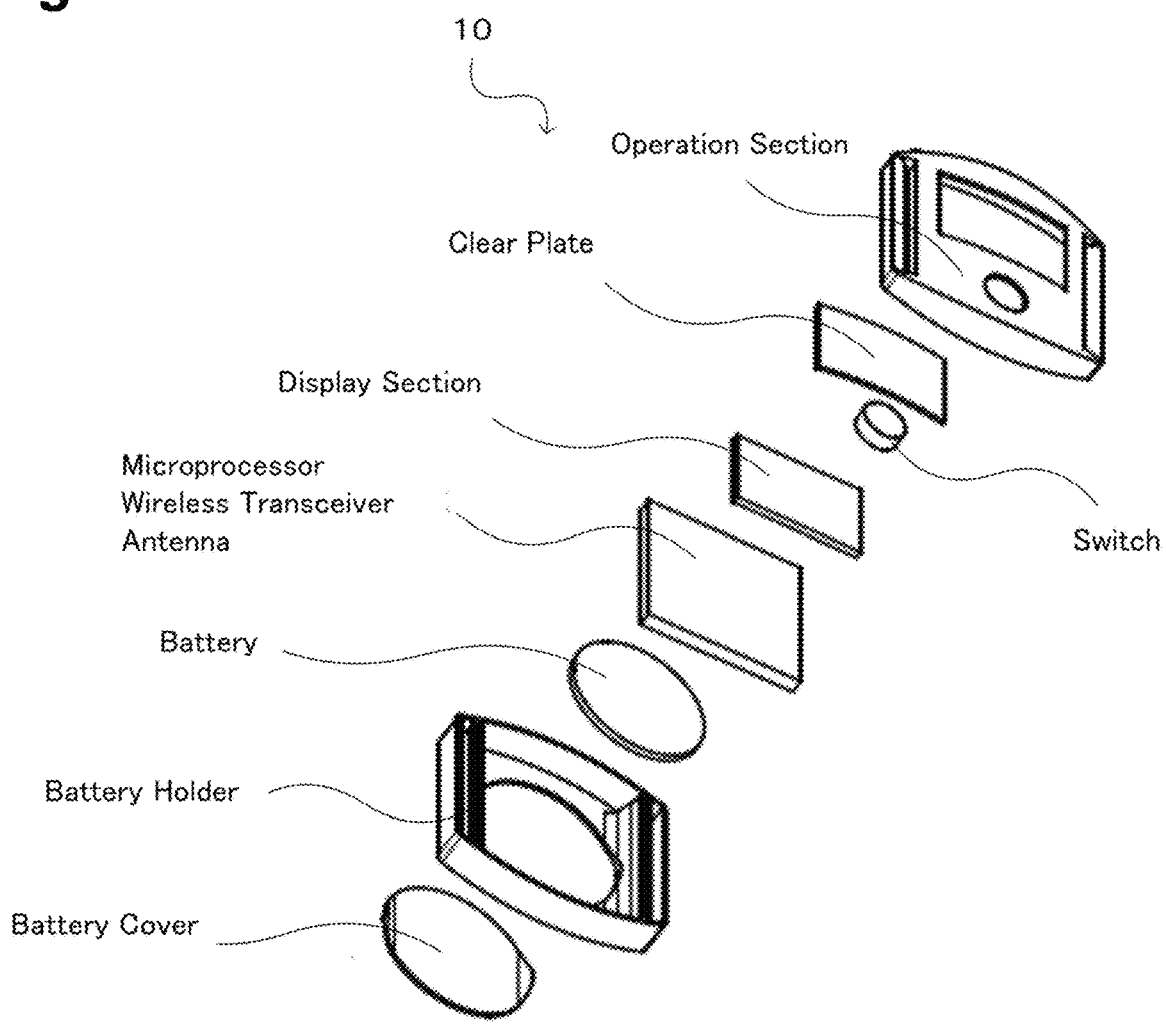
FIG. 2A is a diagram representing the structure of a clinical-thermometer main unit.
Figure 2B:
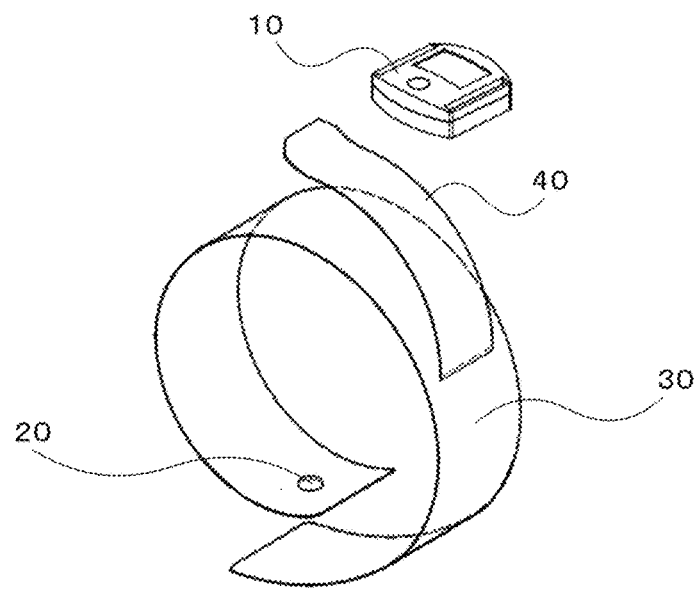
FIG. 2B is a diagram representing the structure of a wearable clinical thermometer.

Reference is made to FIG. 2. FIG. 2 is diagrams representing the structure of a clinical-thermometer main unit, and a wearable clinical thermometer. Herein, the wearable clinical thermometer 1 will be described in detail. As indicated in FIG. 2(*b*), the wearable clinical thermometer 1 involving Embodiment Example 1 is designed as a wristwatch model, and comprises a clinical-thermometer main unit 10, a thermometer main unit fastening belt 40 that retains the thermometer main unit 10, and the belt 30, wherein a temperature sensor configured to sense a target subject's temperature can be fitted detachably from/reattachably onto a location of choice along the inner side of the belt 30.

Further, as indicated in FIG. 2(*a*), built into the clinical-thermometer main unit 10 are basically a microprocessor, which is furnished with a battery, a computation medium, and a storage medium, and a wireless communications transceiver and antenna, wherein the battery supplies electric power to the microprocessor and the temperature sensor.

The clinical-thermometer main unit 10 may be configured so as, in its computation medium, to calculate relationships between base resistance values and actual temperatures, based on calibration coefficients that have been transmitted in, to prepare a resistance—temperature conversion table, and store the resistance-temperature conversion table in the storage medium. With such a table having been prepared, the clinical-thermometer main unit 10 when measuring can obtain a figure for the actual temperature without making the computation every time, but simply by referring to the table, which therefore can serve to curtail the time till the temperature is displayed and reduce costs. Further, the configuration may be rendered to calculate the relationships between base resistance values and actual temperatures based on calibration coefficients estimated beforehand, to prepare a plurality of resistance-temperature conversion tables. A plurality of tables having thus been prepared makes it possible to select an optimal resistance-temperature conversion table corresponding to the calibration coefficients transmitted from the temperature sensor 20.

Further, in cases where a single resistance-temperature conversion table is prepared and stored, re-preparing it by performing computations in accordance with the calibration coefficient value, and storing the table in a rewritable storage device is desirable.

Implementations may enable displaying the measured body temperatures on a dedicated terminal, and outputting (printing, e-mailing, etc.) the chronologically measured temperature data as a chart, and meanwhile enable calling up a past trends graph according to date and time settings. Also, alarms that are auditory or visual, or else both can be established on a per-patient basis. Configuring desired settings is recommendable—e.g., for auditory, selecting from among a terminal's built-in system sounds, or for colors, changing a portion of the screen or the background to a red (yellow) color. Further, unitarily managing temperature data for a plurality of patients with software makes handling easy.

Figure 4:
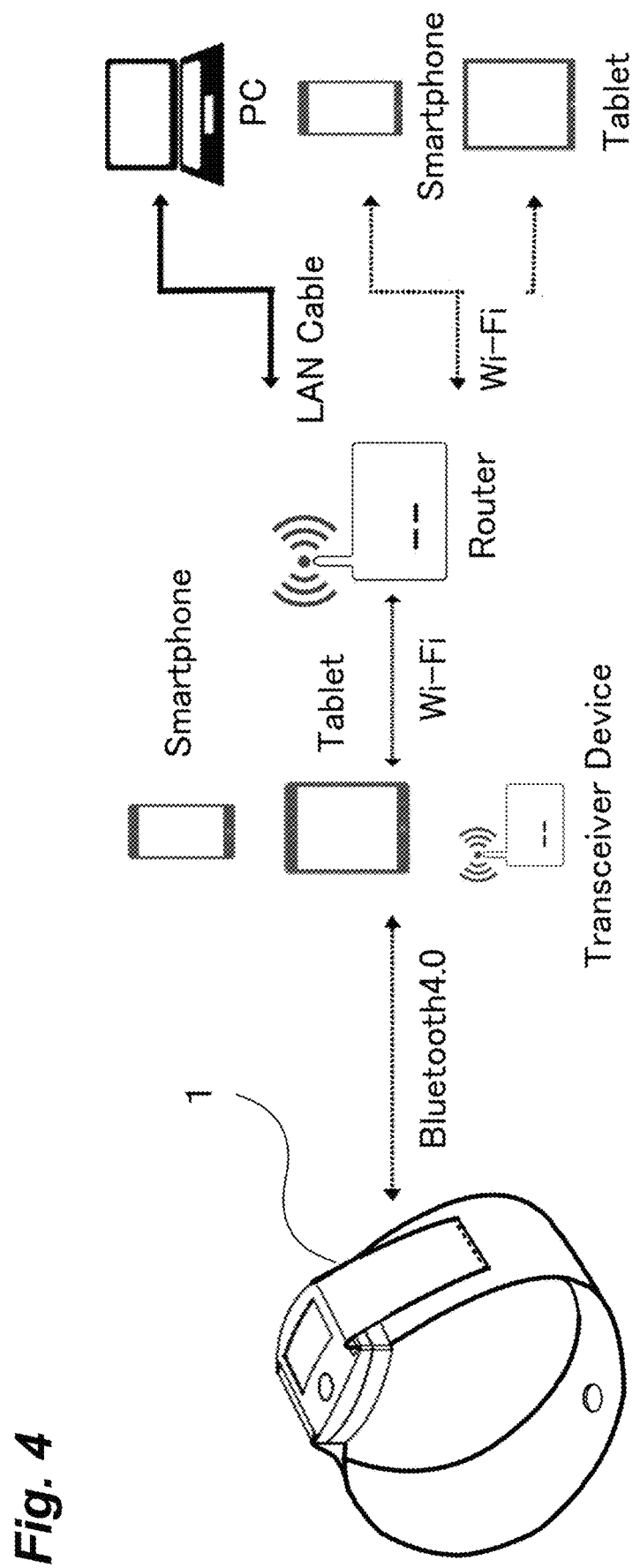
FIG. 4 is a is schematic diagram representing, in a wireless communications transceiver of the thermometer main unit, a different system for receiving body-heat measurement temperatures.
Figure 5:
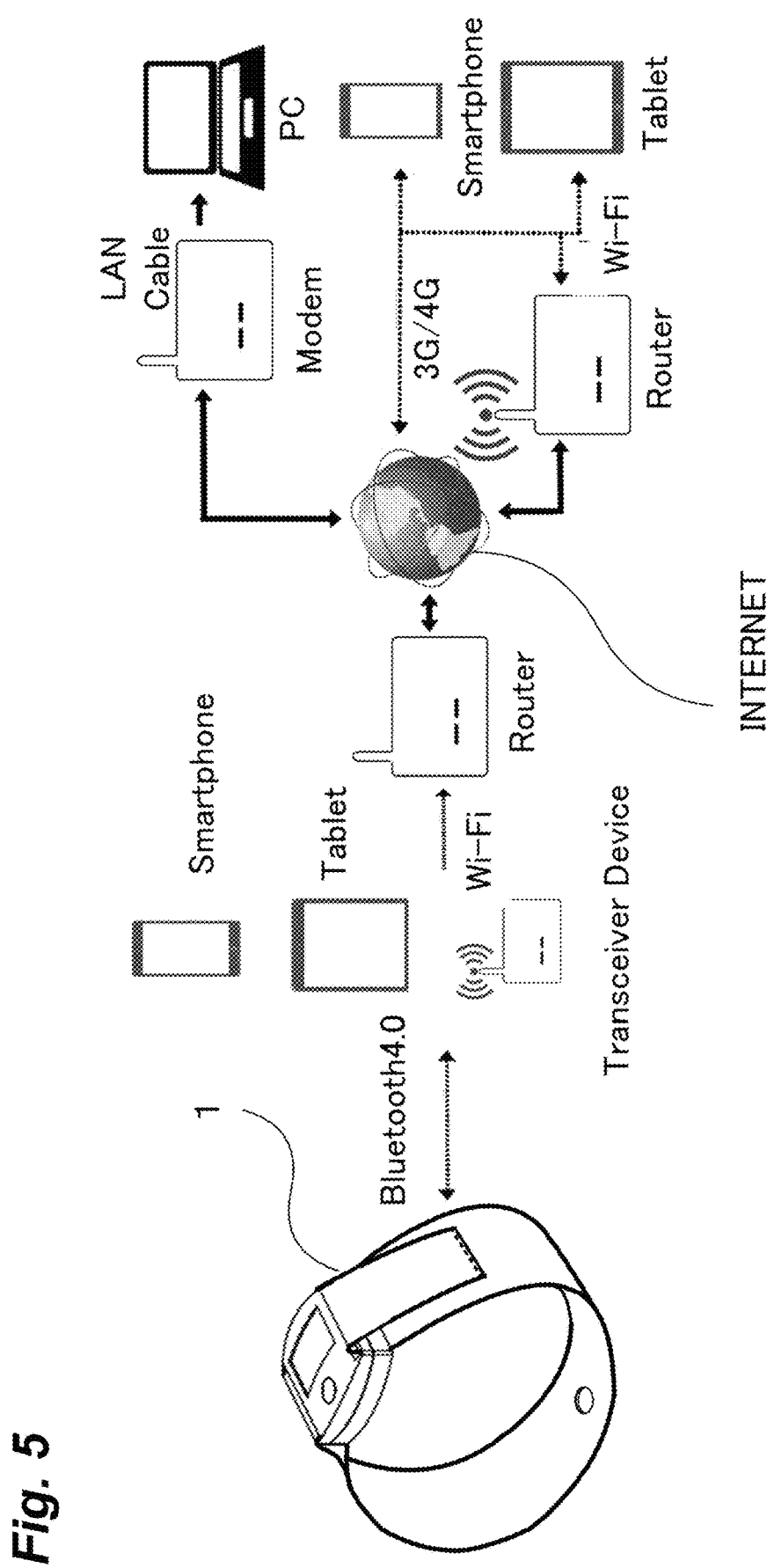
FIG. 5 is schematic diagram representing, in a wireless communications transceiver of the thermometer main unit, a still different system for receiving body-heat measurement temperatures.

FIGS. 3-5 are schematic diagrams representing, in a wireless communications transceiver of the clinical-thermometer main unit 10, an illustrative system for receiving body-heat measurement temperatures. As indicated in FIGS. 3-5, measured body temperature is obtained by reading it out from a dedicated terminal, wherein as the terminal, PCs, smartphones, tablet computers, etc. that may be operated utilizing conforming wireless communications protocols are exemplarily illustrative. The terminal is furnished with a programmable microprocessor that may execute applications, a power source, a display, and a wireless communications transceiver that is two-way communicable with the clinical-thermometer main unit 10. Being able to communicate on the Internet, preferably, or else a local network (LAN) or a wide-area network (WAN) is desirable. The temperature measurements can be obtained in response to a request and/or at preset intervals, and can be stored locally into the memory of the readout device (e.g., smartphone, tablet, portable computer, sensor, etc.).

The clinical-thermometer main unit 10 can be read out from by means of a standard smartphone, tablet, PC, etc. that may operate utilizing a conforming high-frequency/near-field communication NFC wireless protocol as well as the ISO-15693 RFID wireless protocol. For example, in situations where a person wearing the clinical thermometer 1 is sleeping, a physician, nurse practitioner, or other medical professional possessing a smart phone may utilize the smart phone, being high-frequency/near-field communication NFC as well as ISO-15693 RFID compliant, to read out transitions in body temperature of the patient. Near-field communication (NFC) enables smartphones and the like to establish mutual wireless communications by them being brought into contact with each other or otherwise near each other. The NFC standards comprehend communications protocols and data exchange formats, and are based on preexisting radio frequency identification (RFID) standards including ISO/IEC 14443, ISO/IEC 15693, and FeliCa (registered trademark). NFC operates at speeds within a range of from 106 kbit/s to 424 kbit/s at 13.56 MHz, based on the ISO/IEC 18000-3 air interface.

In this way, a physician or nurse practitioner, without having to wake a patient who is wearing the thermometer 1, can at once display in a list, table, chart, etc., in a graphical and/or text-based format, e.g. via a smartphone application or the like, a log in connection with a portion or the entirety of the period during which the wearable clinical thermometer 1 is worn. Accordingly, a log of trends in body temperature is made possible.

The wearable clinical thermometer 1 may be configured so that its wireless communications transceiver is equipped with Bluetooth and NFC, and so that the calibration (compensation) of the temperature sensor 20 is carried out by NFC. Taking advantage of NFC in this way enables calibration of the temperature sensor 20 to be carried out easily by for example simply touching the NFC section of the temperature sensor 20 in the wearable clinical thermometer 1 with a smartphone, without having to go through any number of procedures, input passcodes, etc.

While NFC wireless protocols have been mentioned, it should be understood that various other wireless protocols, including standards-based protocols and proprietary-specification protocols, are usable. For example, any or all among RFID, Bluetooth (registered trademark), Wi-Fi (registered trademark) etc. can be employed.

A description of on-terminal display will be made. To begin with, screen configurations that can be displayed include, as a variety of configuration screens, a device-registration and patient-parameter input screen, a list monitoring screen, a current time display, a body-temperature display, an alarm-settings, patient-name, room-number, and bed-number display, an alarm cutoff button, a selection monitoring screen, a current time display, a trend graph, a display with set-alarm yes/no, alarm cutoff button, and all patient parameters, a callup for a past trends graph according to date and time settings; and also alarm sounds selection, and settings for alarm cutoff time.

Once again, the flow of a method, involving the present invention, of calibrating the temperature sensor 20 will be explained. To begin with, the base-resistance acquisition step (S01) is a step of sampling per the temperature sensor a base resistance value, and acquiring the base resistance value. The sampling is favorably carried out in the temperature sensor attached to the wearable clinical thermometer 1, together with a standard temperature gauge, inside a constant-temperature bath at 37° C.

Next, the computation step (S02) of computing the calibration coefficient is a step of computing a calibration coefficient for calibrating temperature, based on the difference between the base resistance value acquired in the step (S01) of acquiring the base resistance of the temperature sensor 20, and a resistance value gauged with a standard temperature gauge. This exploits being able to find the resistance value from temperature using the thermistor's B constant, and conversely, being able to find temperature from the resistance value.

Then, the calibration coefficient computed in the computation step (S02) is stored (S03) in the measuring-device storage medium.

The calibration coefficient stored in the storage medium in the storage step (S03) is transmitted (S04) to the clinical-thermometer main unit 10.

In the foregoing, preferred embodying modes in temperature-sensor calibration methods of the present invention have been illustrated and explained; however, it should be understood that a variety of modifications are possible without departing from the technical scope of the present invention.

INDUSTRIAL EXPLOITABILITY

A temperature-sensor calibration method of the present invention can be exploited broadly not only in hospitals and medical treatment facilities, but also in clinical thermometers for the home.

LEGEND

1: wearable clinical thermometer
10: clinical-thermometer main unit
20: temperature sensor
30: belt
40: main unit fastening belt
S01: base-resistance acquisition step
S02: computation step
S03: storage step
S04: calibration coefficient transmission step

The invention claimed is:

1. In a wireless-data-communicating wearable clinical thermometer including
    a main unit having a microprocessor, a computation medium, a rewritable memory device, and a wireless communications transceiver, and
    separate from the main unit, a temperature sensor fitted detachably from/reattachably onto the wearable clinical thermometer, for sensing and measuring target-subject body temperature, the temperature sensor having a thermistor, a storage medium, and a near-field communication section, and
    a battery for supplying electric power to the microprocessor and the temperature sensor,
a method for calibrating the temperature sensor, the method comprising:
    a thermistor base-resistance acquisition step of sampling a thermistor base-resistance value per the temperature sensor, and of acquiring the thermistor base-resistance value;
    a computation step of obtaining an actual-temperature resistance value gauged with a standard temperature gauge, the standard temperature gauge being together with the temperature sensor, and, based on a difference between the acquired thermistor base-resistance value and the actual-temperature resistance value gauged with the standard temperature gauge, computing a calibration coefficient for calibrating target-subject body temperature measured by the temperature-sensor thermistor;
    a storage step of storing the calibration coefficient in the temperature-sensor storage medium; and
    a step, in the temperature sensor, of causing the near-field communication section to transmit the calibration coefficient from the temperature-sensor storage medium to the wireless communications transceiver in the main unit of the clinical thermometer.

2. The temperature-sensor calibration method set forth in claim 1,
    further comprising, in the computation medium of the clinical thermometer main unit, a step of preparing a resistance-temperature conversion table by computing, based on the calibration coefficient transmitted from the near-field communication section in the temperature sensor, relationships between the thermistor base-resistance value and actual temperatures, and storing the prepared resistance-temperature conversion table in the rewritable memory device of the clinical thermometer main unit.

3. The temperature-sensor calibration method set forth in claim 2, further comprising, in the computation medium of the clinical thermometer main unit, a step of re-preparing the resistance-temperature conversion table by performing computations in accordance with the calibration coefficient's value, and storing the table in the rewritable memory device of the clinical thermometer main unit.

4. The temperature-sensor calibration method set forth in claim 1, characterized in that
    the clinical thermometer main unit prepares, in the computation medium, a plurality of resistance-temperature conversion tables by computing relationships between the thermistor base-resistance value and actual temperature, based on calibration coefficients estimated beforehand.

5. The temperature-sensor calibration method set forth in claim 1, characterized in that the temperature-sensor thermistor is a negative-temperature coefficient thermistor.

6. The temperature-sensor calibration method set forth in claim 5, characterized in that the calibration coefficient is computed utilizing the thermistor's B constant.

7. The temperature-sensor calibration method set forth in claim 1, further comprising a step of causing the wireless communications transceiver in the clinical-thermometer main unit to transmit to a portable terminal a temperature measurement from the calibrated temperature-sensor thermistor.

8. The temperature-sensor calibration method set forth in claim 1, characterized in that the thermistor base-resistance acquisition step is carried out within a constant-temperature bath, the constant-temperature bath containing the standard temperature gauge.

9. The temperature-sensor calibration method set forth in claim 8, characterized in that the calibration coefficient is computed utilizing the thermistor's B constant.

10. In a system for receiving body-heat measurement temperatures, the system made up of
    a wireless-data-communicating wearable clinical thermometer including
        a main unit having a microprocessor, a computation medium, a rewritable memory device, and a thermometer wireless communications transceiver, and
        separate from the main unit, a temperature sensor fitted detachably from/reattachably onto the wearable clinical thermometer, for sensing and measuring target-subject body temperature, the temperature sensor having a thermistor, a storage medium, and a near-field communication section, and
        a battery for supplying electric power to the microprocessor and the temperature sensor; and
    a terminal furnished with a display and a terminal wireless communications
    transceiver enabling the terminal to be two-way communicable with the clinical-thermometer main unit,
a method for providing the terminal with a calibrated target-subject body temperature measurement from the temperature sensor, the method comprising:
    a thermistor base-resistance acquisition step of sampling a thermistor base-resistance value per the temperature sensor, and of acquiring the thermistor base-resistance value;
    a computation step of obtaining an actual-temperature resistance value gauged with a standard temperature gauge, the standard temperature gauge being together with the temperature sensor, and, based on a difference between the acquired thermistor base-resistance value and the actual-temperature resistance value gauged with the standard temperature gauge, computing a calibration coefficient for calibrating target-subject body temperature measured by the temperature-sensor thermistor;

a storage step of storing the calibration coefficient in the temperature-sensor storage medium;

a step, in the temperature sensor, of causing the near-field communication section to transmit the calibration coefficient from the temperature-sensor storage medium to the thermometer wireless communications transceiver; and a step, in the terminal, of obtaining a calibrated target-subject body temperature measurement from the clinical thermometer.

11. The method according to claim 10, further comprising a step, in the temperature sensor, of causing the near-field communication section to transmit the calibration coefficient from the temperature-sensor storage medium to the terminal wireless communications transceiver.

* * * * *